United States Patent [19]

Saxena et al.

[11] Patent Number: 4,560,649
[45] Date of Patent: Dec. 24, 1985

[54] ASSAYING FOR HLH OR HCG WITH IMMOBILIZED HORMONE RECEPTORS

[75] Inventors: Brij B. Saxena, Englewood; Premila Rathnam, Englewood Cliffs, both of N.J.

[73] Assignee: Cornell Research Foundation, Ithaca, N.Y.

[21] Appl. No.: 440,477

[22] Filed: Nov. 9, 1982

Related U.S. Application Data

[63] Continuation-in-part of Ser. No. 311,736, Oct. 15, 1981, abandoned.

[51] Int. Cl.[4] .................... G01N 33/54; G01N 33/74; G01N 33/76
[52] U.S. Cl. .................... 435/7; 260/112 R; 435/181; 435/810; 436/501; 436/527; 436/805; 436/810; 436/817; 436/818
[58] Field of Search .................... 435/7, 181, 188; 436/501, 527, 805, 810, 817, 818

[56] References Cited

U.S. PATENT DOCUMENTS 3,654,090 4/1972 Schuurs .
4,016,250 4/1977 Saxend .
4,094,963 6/1978 Saxend .
4,231,999 11/1980 Carlsson .................... 436/804 X

OTHER PUBLICATIONS

Van Weeman, B. K. et al., Febs Letters, 15(3), 232-236, (Jun. 24, 1971).
Engvall E. et al., Immunochemistry, 8(9), 871-874, (Sep. 1971).
Kawaoi, A. et al., Fed. Proc. 32, 840 Abs., Abstract No. 3508, (1973).
Saxend, B. B. et al., "Psychoneuroendocrinology in Reprod.", L. Zichella et al., eds., 277-288, Elsevier, 1979.
Carlsson, J. et al., Biochem. J., 173(3), 723-737, (1978).
Jibiki, K. et al., Acta Endocrinologica, 87, 838-844, (1978).
Saito, T. et al., J. Clin. Endocrinol. & Metabolism, 43(5), 1186-1189, (1976).
Post, K. G. et al., J. Clin. Endocrinol. & Metabolism, 50(1), 169-175, (1980).
"Enzyme Labelled Immunoassay of Hormones and Drugs", Pal, S. B., ed., Khan, S. F. et al., 257-275.
Walter de Gruyter & Co., Berlin, 1978.
Dattatreyamurthy, B. et al., "Functional Correlates of Hormone Receptors in Reproduction", Mahesh et al., eds., pp. 397-411, Elsevier, North Holland, 1980.
Charreau, E. H. et al., J. Biol. Chem., 249(13), 4189-4195, (1974).
Haour, F. et al., J. Biol. Chem., 249(7), 2195-2205, (1974).
Rebois, R. V. et al., Proc. Natl. Acad. Sci. USA, 78(1), 2086-2089, (Apr. 1981).
Metsikko, K. et al., Biochim. Biophys. Res. Comm., 95(4), 1730-1736, (1980).
Dufau, M. L. et al., J. Biol. Chem., 248(20), 6973-6982, (1973).
Dufau, M. L. et al., Biochim. Biophys. Acta, 278, 281-292, (1972).
Jacobs, S. et al., Proc. Natl. Acad. Sci. USA, 76, 4918-4921, (1979).
Krupp, M. N. et al., Nature, 278, 61-62, (Mar. 1979).
Ji, I. et al., Proc. Natl. Acad. Sci. USA, 77(12), 7167-7170, (Dec. 1980).
Patrick, J. et al., Biochem. Biophysical Res. Comm., 64(1), 219-225, (1975).
Wimalasend, J. et al., Endocrinology, 110, 1004-1012, (1982).
Bauknecht, T. et al., Acta Endocrinologica, 96, 122, Abst. 125, (1981).
Haga, T. et al., J. Biol. Chem., 252(16), 5776-5782, (1977).
Penn, A. S. et al., Ann. N.Y. Acad. Sci., 274, 354-376, (1976).
Chemical Abstracts, I, 96:139249p, (1982).
Chemical Abstracts, II, 97:138772n, (1982).

Primary Examiner—Sidney Marantz
Attorney, Agent, or Firm—Sughrue, Mion, Zinn, Macpeak & Seas

[57] ABSTRACT

A method to obtain a substantially pure and stable hLH-hCG receptor from gonadal cells is disclosed. The characteristics of the purified receptor are disclosed. The receptor, in addition to being used as receptor in an enzyme- or dye-receptor assay for hLH and/or hCG, can be used to purify hLH or hCG used in the preparation of standard dye-hormone or enzyme-hormone complexes. These complexes can be used in enzyme- or dye-immunoassays, as well as the receptor assay.

68 Claims, 1 Drawing Figure 4,560,649

ASSAYING FOR HLH OR HCG WITH IMMOBILIZED HORMONE RECEPTORS

The invention described herein was made in the course of work under a grant or award from the Department of Health and Human Services.

This application is a continuation-in-part application of Ser. No. 311,736, filed Oct. 15, 1981 now abandoned.

BACKGROUND OF THE INVENTION

For various reasons, it is highly desirable to be able to qualitatively and/or quantitatively measure human luteinizing hormone (hLH) and human chorionic gonadotropin (hCG) in a convenient, reliable manner. For example, it is known that the concentration of hLH in female biological fluids increases dramatically just prior to ovulation. A convenient, qualitative detector of the hLH surge for "at home" use could pinpoint the time of ovulation for women with fertility problems and/or aid in fertility regulation. Also, a quantitative hLH assay, which could be used by the physician in the office would be useful in the medical evaluation and observation of various conditions associated with hLH presence and/or concentration variation.

Similarly, significant presence of hCG in the female biological fluids has been accepted as one of the most reliable tests confirming pregnancy. hCG is secreted by the developing blastocyst and can be detected in pregnant women as early as 7 to 9 days after fertilization. Again, a qualitative "at home" pregnancy test capable of providing a reliable result within the first two weeks of pregnancy would be extremely useful. Also, a convenient assay procedure usable by the practicing physician would prove of benefit in the diagnosis and evaluation of various abnormal conditions characterized by hCG levels, such as in the diagnosis of ectopic pregnancy and spontaneous abortion, and in the follow-up of patients with trophoblastic disease and infertility problems.

One aspect of the present application is concerned with improved solid phase assay systems and methods for measuring hLH and/or hCG, which do not require radioactive substances. In one embodiment of the present invention, an enzymatic marker is employed. In another embodiment, a direct dye marker is used to eliminate the step of reacting enzyme with its substrate for measurement. Another aspect of the present application is concerned with materials and reagents to be used in the improved assay systems and methods.

Van Weeman et al, "Immunoasssay Using Antigen-Enzyme Conjugate", *FEBS LETTERS*, 15:232 (1971), conjugated hCG to horseradish peroxidase through glutaraldehyde and then used the conjugate for enzyme-immunoassay of hCG. A solid phase assay procedure is disclosed by Van Weeman et al where hCG antibody is attached to a cellulosic support (reprecipitated and diazotized m-aminobenzyloxymethyl cellulose or microcrystalline cellulose activated by CnBr.) Also, see U.S. Pat. No. 3,654,090 using the Van Weeman conjugate in similar assay procedures. Another enzyme used in the art in place of horseradish peroxoidase is alkaline phosphatase (ALP). For example, see Engvall et al, "Enzyme-linked Immunoabsorbent Assay (ELISA), Quantitative Assay of Immunoglobulin G", *Immunochemistry*, 8:871 (b 1971). Kawaoi et al, "An Improved Method of Conjugation of Peroxidase with Protein". *Fed. Proc.*, 32 Abstract 840 (1973) also disclose a method for forming an enzyme-hormone complex.

Saxena et al, "Development of a Solid-Phase Centrifugation-free Enzyme Assay for LH for Ovulation Detection", *Psychoneuroendocrinology in Reproduction*, Zichella et al, editors, Elsevier/North Holland (1979), p. 277, describe both an enzymeimmunoassay and an enzymereceptorassay for hLH using antibody-coupled glass beads or receptor-coupled glass beads, respectively (glutaraldehyde activated aminopropyl glass beads) and an hLH-alkaline phosphatase conjugate (4-azidobenzoyl derivative of hLH). The receptor used by Saxena et al was of relatively low yield and suffered from poor stability.

Carlsson et al, "Protein-Thiolation and Reversible Protein-Protein Conjugation", *Biochem. J.*, 173:723 (1978), disclose that N-succinimidyl 3-(2-pyridyldithio) propionate (SPDP) can be employed as a heterobifunctional reagent in forming protein-protein conjugates through a disulfide link. As one example, Carlsson et al form a horseradish peroxidase-rabbit anti- (human transferrin) antibody conjugate. In general, 2-pyridyl disulfide structures are introduced into both the peroxidase and the antibodies by their reaction with SPDP. Although either of the 2-pyridyldisulfide moieties can be converted into the corresponding thiol derivative by specific reduction with dithiothreitol at pH 4.5, Carlsson et al formed the thiolated antibodies and reacted them with the peroxidase 2-pyridyl disulfide derivative by thiol disulfide exchange to produce the peroxidase enzyme-antibody conjugate.

It is also known that hLH and hCG consist of two noncovalently linked polypeptide chains classified as $\alpha$ and $\beta$ subunits. The $\alpha$ subunits of these glycoprotein hormones, as well as the $\alpha$ subunits of other glycoprotein hormones, have almost identical amino acid sequences and are practically indistinguishable immunochemically. In contrast, the $\beta$ subunits of each have their own distinctive amino acid sequences which differentiate them from the $\beta$ subunits of the other glycoproteins. Methods are known to purify antibody, such as hCG $\beta$ antiserum, to reduce cross-reactivity with hCG $\alpha$ subunits or with similar hLH subunits. For example, see Jibiki et al, "A Receptor-Immunoassay for the Determination of the Specificity of Anti-hCG-$\beta$ Sera", *ACTA Endocrinologica*, 87, 838 (1978), where hCG-$\beta$ antisera is purified by immunoabsorption with hLH and hCG-$\alpha$.

Saito et al, "Use of Receptors in the Preparation of LH-Free Serum", *J. Clin. Endocrinol. Metab.* 43:1186 (1976), used purified gonadotropin receptor to bind serum hLH to the exclusion of other serum proteins. This general technique provides a purer serum, depending upon the specificity of the receptor.

Glass beads have been used as the solid phase in the radioimmunoassay of hormones such as hLH and hCG. See Post et al, "A Rapid, Centrifugation-Free Radioimmunoassay Specific for Human Chorionic Gonadotropin Using Glass Beads as Solid Phase", *J. Clin. Endocrinol. Metab.*, 50:169 (1980), where solid glass beads of 6 mm diameter were sandblasted and then heated in the presence of $\gamma$-aminopropyltriethoxysilane to generate reactive alkylamino groups on the glass surface. The amino groups are activated with glutaraldehyde and subsequently hCG-$\beta$ antibody is covalently coupled thereto.

Finally, a key reagent in an hLH or hCG receptor assay is the receptor itself. Heretofore, large quantities of the common hLH and hCG receptor of the corpora lutea have not been obtained in sufficiently pure form for use in enzyme receptor assays of good reliability and accuracy. See Khan et al, "Use of Purified Gonadotropin Receptor in the Development of an Enzyme Receptorassay (ERA) for Luteinizing Hormone (LH) and Human Chorionic Gonadotropin (hCG)", *Enzyme Labelled Immunoassay of Hormones and Drugs,* S. B. Pal, editor, de Gruyler & Co. (1978).

A number of the steps used in the receptor purification system of the present invention, the present invention resulting in a good yield of a receptor having better stability and higher purity, were disclosed by the inventors in the symposium paper. "Current Status of the Purification and Characterization of LH-hCG Receptors," *Functional Correlates of Hormone Receptors in Reproduction,* Mahesh et al, editors, page 397, Elsevier North Holland (1980), presented Oct. 15, 1980.

U.S. Pat. No. 4,016,250 and as a divisional thereof, U.S. Pat. No. 4,094,963, both to Saxena, disclose receptorassay methods for determining hCG and/or hLH in a biological fluid wherein binding of said hCG and hLH in the sample is with a plasma membrane extract from the corpus luteum of a species possessing the common receptor for hCG and hLH. The additional purification steps disclosed herein, as compared to the Saxena patents, result in the preparation of a receptor material of significantly higher purity and binding capacity.

SUMMARY OF THE INVENTION

It is an object of the present invention to provide improved solid phase receptor-based and antibody-based assays for qualitatively detecting hLH or hCG.

Another object of this invention is to provide improved solid phase receptor-based and antibody-based assays for quantitatively determining hLH or hCG level.

A further object of this invention is to provide "at home" tests usable by women to detect ovulation or pregnancy in a reliable, convenient manner.

Still another object of this invention is to provide improved solid phase assays for hLH and hCG which can be used in a quantitative fashion by the practicing physician in his office.

Another object of this invention is to provide an improved, substantially pure hLH and hCG receptor, and a process for obtaining it.

A further object of this invention is to provide an improved enzyme-hormone conjugate and processes for obtaining it.

In accordance with the present invention, a substantially pure and stable hLH-hCG receptor is obtained from bovine corpora lutea, in large yields, through the use of a novel, sequential concentration and purification method. This novel, substantially pure gonadotropin receptor is not only used as a receptor in the enzyme receptorassay embodiment of this invention but can also be used to purify hLH and hCG so that substantially pure hormone is used in the preparation of enzyme-hormone complexes used as standard reagents in both the enzyme receptor assay (hereinafter "ERA") and the enzymeimmunoassay (hereinafter "EIA") of this invention. It is preferred to use the enzymeimmunoassay approach (specific antibody instead of receptor) in the pregnancy test based on hCG level since some hLH would also be present in the patient's fluids. The enzyme receptorassay is specific for the ovulation detection test embodiment since hCG should not be present in significant quantities in the healthy non-pregnant woman. Of course, both EIA and ERA can be used for hCG or hLH detection. hLH in pregnancy would be of a very low level.

In one embodiment of the present invention, a known, predetermined amount of hLH-enzyme conjugate is incubated with a reactive quantity of receptor coupled to a solid phase, such as glass beads, in the presence of the standard or unknown. The receptor level is sufficient to be reactive with the expected surge level of hLH at ovulation. Upon separation of the solid phase from the supernatant containing any unreacted or displaced hormone-enzyme conjugate and subsequent measurement of the enzyme by its catalysis of a color-forming reaction, a color is formed in the supernatant indicating ovulation or less color is formed in the solid phase since a proportionate amount of the conjugate bound to the solid phase will be displaced by the hLH.

An analogous "at home" test for pregnancy can be based on hCG detection. However, in the pregnancy test, it is preferred that purified hCG $\beta$ antibody be used in place of the receptor because of the presence of some hLH in the body fluids which would also react with receptor.

Other variations of the invention will become apparent from the Detailed Description of the Invention hereinafter.

DESCRIPTION OF THE DRAWING

The FIGURE of the Drawing is a flow diagram of a specific example of the receptor purification method of this invention.

DETAILED DESCRIPTION OF THE INVENTION

Receptor Preparation

Figure 1:
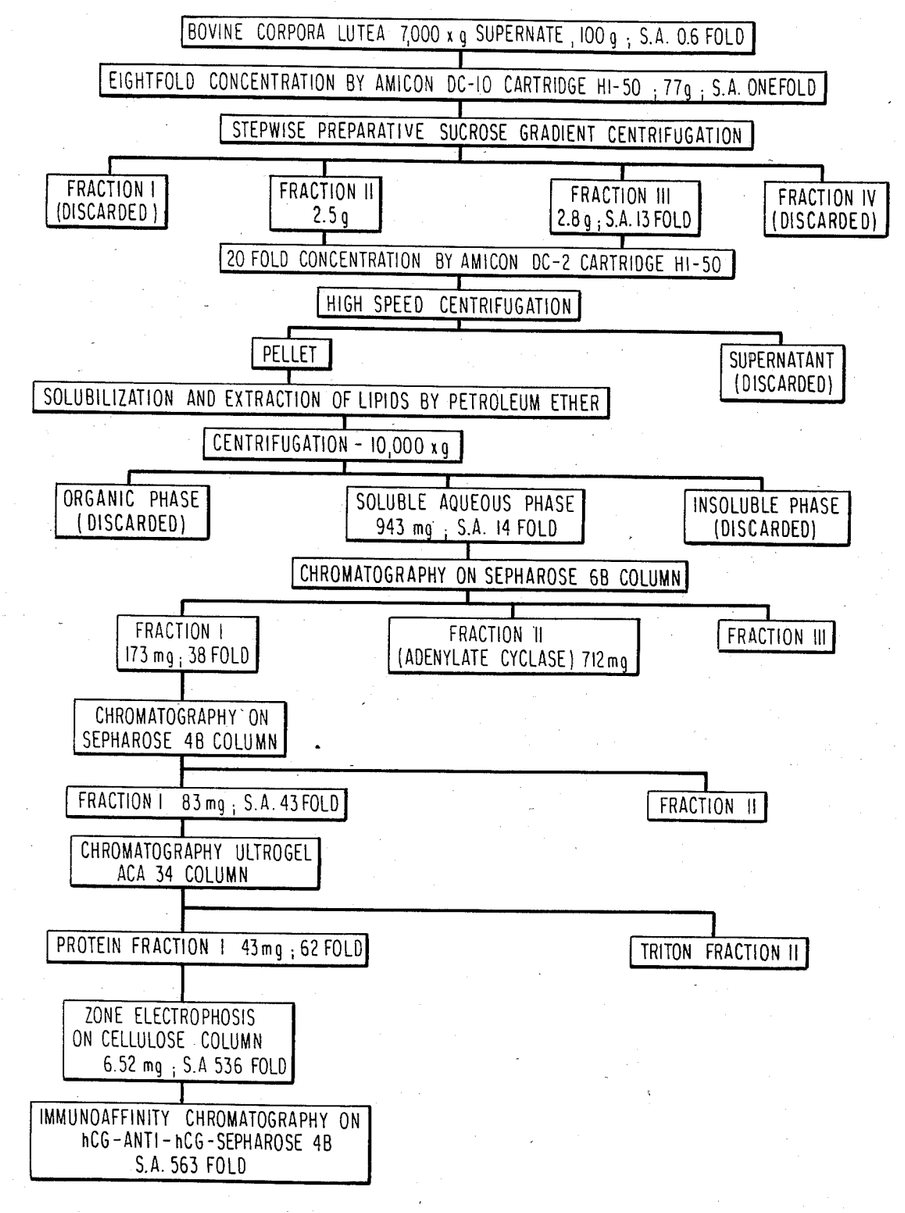

The FIGURE of the Drawing is a flow diagram of a specific example of the receptor preparation method of this invention.

The receptors for hLH and hCG are the same and are located in the plasma membrane of the endocrine responsive gonadal cells.

The above-referenced "Functional Correlates of Hormone Receptors in Reproduction" describes some of the prior art work in this field.

The receptor purification method of this invention will be described with reference to the use of bovine corpora lutea as the starting material. It is expected that other known receptor source materials such as rat Leydig cells, pseudopregnant rat ovaries and so on could be substituted for the bovine corpora lutea. Bovine corpora lutea was chosen to provide greater amounts of receptor compared with other source material.

Previous work had shown that the receptor is relatively insoluble, but detergent-solubilizable in aqueous media. In this work, a supernate from a bovine corpora lutea homogenate was used as the starting material. Corpora lutea are homogenized for 15 to 20 seconds in a Tris-HCl buffer, containing 15% sucrose in a tissue to buffer ratio of 1:10 (w:v) to yield a homogenate which is centrifuged for 30 minutes at 1,000 rpm to remove cell debris. The supernate is then centrifuged at 7,000×g to yield a sediment and a supernate, both containing receptor. In practice, the sediment has a binding capacity nearly 5 times that of the supernate and is used in the preparation of Biocept-G ® radioreceptorassay pregnancy test kits by Wampole Laboratories, Princeton, N.J. The supernate, which would otherwise be discarded, is used as the starting material herein. Obviously, the more active sediment could be detergent solubilized and/or combined with supernatant and/or the supernatant from the 1,000 rpm centrifugation could be employed as a receptor source material. Although in the specific example hereinbelow, a 7,000×g supernate was employed, obviously other solubilized fractions could be employed and conveniently tested for the presence of the receptor through a radioimmunoassay or similar technique.

The liquid fraction, after separation from the homogenate is concentrated by ultrafiltration. A HI-50 hollow fiber cartridge (cutoff level of 50,000 molecular weight) was employed in an AMICON DC-10 unit, available from Amicon of Lexington, Mass. to remove an inhibitor of hormonereceptor binding and inert proteins of below 50,000 molecular weight. This step yields a concentrated supernatant. Previous work had estimated the molecular weight of the receptor to be within the 110,000 to 115,000 range.

Next, the concentrated supernatant is fractionated, primarily to remove high density inactive protein and light density lipid. Preparative sucrose linear density gradient ultracentrifugation has been found to be a useful technique to separate inactive materials from the receptor. Using a linear sucrose gradient from 35% to 10%, it was found that the fractions eluted between 18-28% sucrose gradient contained nearly all of the active receptor.

Since the sucrose should be removed, ultrafiltration is again carried out followed by ultracentrifugation to yield a sediment containing the receptor material.

In order to remove additional extraneous lipid materials, further separatory purification is carried out by re-dispersing the sediment in water with the aid of a surface active agent (detergent) and extracting with an organic solvent such as petroleum ether. Following extraction, which mostly removes neutral lipids and low affinity-high capacity binding sites, the aqueous phase is separated from any insoluble residue. It is believed that other organic solvents could be tried in place of the petroleum ether and some of them would function in an equivalent manner to petroleum ether. However, the present inventors have found that ethanol, methanol, carbon tetrachloride and butanol do not perform in a satisfactory manner.

Our earlier work and the literature contains evidence that the hLH-hCG receptor consists of a binding subunit and an associated subunit of an adenyl cyclase and that these subunits can be readily separated by sucrose density gradient centrifugation, and Sepharose-6B chromatography of the detergent solubilized receptor, Khan et al, supra. Since it is also necessary to separate out the surface active agent from the receptor and to purify the receptor further, multi-stage gel filtration/chromatography was carried out to separate the binding fraction from the adenylate cyclase activity fraction, from the majority of the 5'-nucleotidase activity and from the surface active agent.

Additional protein separation was then carried out using electrophoresis, more specifically in the example herein vertical zone electrophoresis on a cellulose column. Zone electrophoresis on a cellulose block has been tried with some success but does not appear useful for large scale purification. The active fractions were combined and re-chromatographed. Finally, immunoaffinity column chromatography on hCG bound-hCG antibody directly coupled to the chromatography matrix was carried out to complete the purification of the receptor material. Since in work to date the immunoaffinity column chromatography increases activity only slightly, the zone electrophoresis product may have reached a practical limit of purity. Direct affinity chromatograph and indirect immunoaffinity chromatography can be used in place of electrophoresis, but to date protein recovery has been too low from a practical standpoint. These procedures result in the preparation of a purified receptor protein similar to that obtained from zone electrophoresis, but different in amino acid analysis. In addition, it is not believed that the products obtained by either of the affinity chromatography procedures is electrophoretically homogenous ("electrophoretically pure")

The following example illustrates preparation of the improved receptor of this invention. In this example, a detergent (Triton X-100) was used to solubilize the receptor protein. Through experimentation we found that a minimum concentration of 0.35% Triton X-100 was necessary to keep the receptor in a soluble state at a concentration of 240 mg protein per ml.

EXAMPLE 1

1200 bovine ovaries stored at $-60°$ C. were thawed. The corpora lutea therefrom were homogenized for 15 to 20 seconds in 0.1M Tris-HCl buffer (pH 7.4 buffer containing 1 mM each of $CaCl_2$, $MgCl_2$ and dithiothreitol, 0.01% sodium azide, $10^{-6}$M phenymethylsulfonyl fluoride and 100 μg/ml soya bean trypsin inhibitor containing 15% sucrose in a tissue to buffer ratio of 1:10(w:v). The homogenate was centrifuged for 30 minutes in 8 one liter capacity swing-out buckets at 1000 rpm (Sorvall, Newton, Conn.). The supernate was recentrifuged at 7,000×g for 45 minutes. The yield was 100 grams of protein. The 7,000×g supernate was concentrated 8-fold by an Amicon DC-10 unit equipped with Hl-50 hollow fiber cartridbe (Amicon, Lexington, Mass.) suspended in an equal volume of the Tris-HCl buffer, reconcentrated to the original volume to reduce sucrose concentration and stored in 200 ml aliquots at $-60°$ C. (All temperature values herein are centigrade unless stated otherwise.) The yield at this stage was 77 grams of protein. This concentrate can be diluted with buffer and reconcentrated.

Next, the above obtained concentrated supernate was fractionated by a linear sucrose density gradient centrifugation. This was accomplished by preparative fractionation of aliquots of 200 ml each (20 g protein) of the concentrated 7,000×g supernate in a Beckman Model L2-65B refrigerated ultracentrifuge, using a 1.6 liter capacity rotor (Ti-50). A linear sucrose gradient from 35% to 10% was prepared by the aid of a Beckman gradient pump (Model No. 141). The sample was layered on top of the sucrose gradient, the rotor was accelerated to 30,000 rpm and the centrifugation was continued for two hours. The rotor was then decelerated to maintain 3,500 rpm. The sucrose density gradient was eluted by displacement with a 40% sucrose solution and 20 ml fractions were collected every 0.5 minute. Fractions were analyzed for specific binding by $^{125}$I-hCG. Two fractions eluted between 18% to 28% sucrose contained nearly all of the active receptor. Sucrose concentration was measured by refractive index. The obtained fractions totaled 6.2 g protein.

Thereafter, the two fractions were separately concentrated by an Amicon DC-2 unit equipped with a HI-50 cartridge. Then, the samples were diluted with the Tris- HCl buffer and re-concentrated in the same apparatus. Finally, this phase of the purification process was completed by centrifuging at 55,000 rpm for 4 hours to sediment the receptor protein. Percent recoveries for the two fractions were 60% and 92%, respectively. The sediments are combined at this point. The 10 mM Tris-HCl buffer, containing 0.5% Triton X-100 was added to the receptor fraction (25 mg protein per ml). 1% Triton X-100 solubilized more protein but significantly reduced hormone binding activity, perhaps due to formation of Triton X-100 micelles. The suspension was sonicated at 50 watts, four times for 5 second duration each time at 4° C. to increase receptor protein solubilization and recovery of hormone-binding activity. The neutral lipids were extracted by shaking with an equal volume of chilled petroleum ether at 4° C. for one hr and finally centrifuging at 10,000 rpm for one hr. The organic solvent, the aqueous phase, and the insoluble residue were separated. The aqueous phase contained the solubilized receptor.

The aqueous layer was recentrifuged at 5,000 rpm and 943 mg of protein recovered. This product was purified by gel filtration on a column of Sepharose-6B. The column was eluted with the Tris-HCl buffer, containing 0.5% Triton X-100 at a flow rate of 13.5 ml per hour. Six ml fractions were collected and tested for receptor using $^{125}$I-hCG, the fractions having significant receptor activity being pooled and then fractionated on multiple 2.8×35 cm columns of Sepharose-4B. It was found that the ascending chromatography on Sepharose-6B separated a large amount of the adenylate cyclase activity (retarded protein fraction) from the hormone binding activity (unretarded protein fraction). The sample at this point contained 22 mg protein per 15 ml of the Tris-HCl buffer. Column elution was carried out using the Tris-HCl buffer containing 0.5% Triton X-100 at a flow rate of 8 ml per hour. 4 ml fractions were collected. In essence, the fraction obtained from the Sepharose-6B column was sub-divided into two fractions by the Sepharose-4B columns, one fraction containing most of the hormone binding activity (unretarded protein fraction) and the other fraction containing most of the 5'-nucleotidase activity (retarded fraction). Again, through testing by specific binding to $^{125}$I-hCG, the active fractions were pooled. The active fractions from four Sepharose-4B columns were concentrated 5-fold by an Amicon ultrafilter and gel-filtered through a 5×50 cm column of Ultrogel-ACA-34 (LKB Instruments).

The Ultrogel-ACA-34 column was eluted with 0.3M lithium borate buffer (1 mM MgCl$_2$, 0.01% NaN$_3$ and 0.5% Triton) pH 7.2 at a flow rate of 10 ml/hr. 4 ml fractions were collected. The Ultrogel-ACA-34 significantly reduced the Triton-X-100 concentration, ex. from about 0.5% to about 0.2%.

At this point, the sample consisted of 73.5 mg of protein in the lithium-borate buffer. Vertical zone electrophoresis was carried out on a 3×42 cm column of cellulose. The cellulose powder was equilibrated in the lithium borate buffer, decanted and then packed into the column. The column was washed extensively with the same buffer prior to electrophoresis. The receptor protein was equilibrated in the same buffer by dialysis. The conditions of electrophoresis were 60–80 mA, 300–315 volts, 72 hours duration. In another procedure, a constant voltage of 300 volts and 60 mA for 5 hours at 4° C. was used. The column was eluted with the lithium borate buffer. Fractions containing the receptor were concentrated by ultrafiltration and chromatographed on Ultrogel ACA-34 columns in the lithium borate buffer to remove excess Triton and to concentrate into a smaller volume. At this stage, the purified product weighed 6.52 mg. The binding capacity of the original 7,000×g supernate, the first Ultrogel fraction and the product at this stage were 5.15, 310 and 2,681 pMhCG/mg protein (affinity constant (Kd) of 0.76×10$^{-10}$ liter M$^{-1}$), respectively, which represents approximately an 11,805-fold purification of the protein in the 7,000×g supernate and a final 536-fold increase in receptor binding capacity.

A further purification step was carried out by immunoaffinity column chromatography on 'hCG bound anti-hCG Sepharose-4B matrix. The receptor specific activity as compared to the zone electrophoresis product increased only by 1.05 fold.

Molecular weight of the electrophoretically pure receptor glyco protein was found to be about 5.9 million using gel permeation chromatography, as described more fully hereinafter. Purification has advanced to the degree that analysis of the receptor material by disc-gel electrophoresis following treatment hereinafter disclosed yielded a single glycoprotein-band, of about 240 thousand molecular weight. (All molecular weights, amino acid analyses and carbohydrate analyses of the receptor protein and components thereof disclosed herein are understood to be within the normally accepted error of ±10% of the value disclosed) Various protein markers were used to estimate the aggregate molecular weight as well as the molecular weights of the various aggregate sub-units disclosed hereinafter. Accordingly, one embodiment of this invention involves the discovery of an electrophoretically homogeneous hLH-hCG receptor glycoprotein of about 5.9 million molecular weight composed of a plurality of glyco polypeptide components, probably linked to one another through di-sulfide bonds to form said glycoprotein aggregate, said glycoprotein aggregate component appearing as a single glycoprotein band as determined by disc-gel electrophoresis.

Although it is believed that the isolated receptor could be obtained from the corpus luteum of various species of animals having the common receptor for hLH and hCG, as well as from other receptor sources such as those disclosed hereinbefore (and also could be synthetically produced following further structural analyses such as amino acid sequence) the present inventors obtain it from bovine corpora lutea. Thus, a more specific embodiment of this aspect of the invention involves a detergent solubilizable, electrophoretically pure, hCG-hLH receptor glycoprotein of bovine corpora lutea, as above defined, and having a specific binding capacity of at least 2000 pM hCG/mg protein, preferably at least 2500 pM hCG/mg protein. Binding capacity was performed by equilibration of the protein sample with approximately 50,000 cpm equivalent to 1.25 ng of $^{125}$I-hCG, in the presence of increasing concentrations of unlabeled hCG from 0.25 to 20,000 ng. Conventional incubation procedures were used, with the addition of an equal volume of 20% (w/v) polyethylene glycol 6,000, dissolved in phosphate buffered saline, to the incubate to precipitate the hormone-receptor complex. Thereafter, the tubes were shaken, centrifuged and the supernate aspirated. Sediments were resuspended in buffer, again mixed with the polyethylene glycol and recentrifuged. Radioactivity of the pellet, representing $^{125}$I-hCG receptor complex was determined. Specific binding and affinity constants were calculated according to the method of Scatchard, G, *Ann. N.Y. Acad. Sci.*, 51, 660 (1949).

Disc-gel electrophoresis was carried out using sodium dodecyl sulfate (hereinafter "SDS")-polyacylamide gel disc electrophoresis as follows:

The purified hLH-hCG receptor fraction was analyzed by SDS-polyacrylamide disc-gel electrophoresis, according to the method of King and Laemmli, *J. Mol. Biol.*, 62, 465 (1971) with minor modifications, to yield an optimum resolution of protein components. Aliquots of 30–60 mg of purified fractions of the hLH-hCG receptor were solubilized in 0.5% Triton X-100, lyophilized and dissolved in 100 ml of water. Samples were then dialyzed for 48 hours against 0.125M Tris-HCl buffer of pH 8.0, containing 1 mM EDTA. Samples were heated in boiling water in the presence of 2% SDS alone or 2% SDS and 1% mercaptoethanol (M.E.), for $1\frac{1}{2}$ minutes. Protein markers of known molecular weights dissolved in Tris-HCl buffer and treated with 2% SDS and 1% M.E. were applied on the stacking gel and electrophoresed simultaneously. The electrophoreses were performed in 0.025M Tris-glycine buffer containing 0.1% SDS, pH 8.3. After the electrophoreses, the gels were removed from the glass columns and the protein bands were stained with Coomassie-Blue. The relative mobilities ($R_f$) of the protein markers and of the purified receptor fractions were calculated, and a relationship was established between the $R_f$ and logarithm of molecular weight of each marker protein, to calculate the molecular weights, of the purified receptor samples. The 5.9 million aggregate sample treated with 2% SDS yielded a single glycoprotein band of approximately 240,000 molecular weight. The sample treated with SDS plus M.E. yielded three bands of approximately 160,000; 57,000 and 44,000 molecular weights, suggesting the presence of oligomers, probably disulfide linked.

Prior to disc-gel electrophoresis, the receptor protein obtained after cellulose zone electrophoresis was subjected to gel permeation chromatography on a column of Sepharose-4B to determine molecular weight. After gel filtration, the unretarded fraction of receptor protein is the 5.9 million molecular aggregate, as above disclosed. The column was eluted with 10 mM Tris-HCl buffer containing 1 mM MgCl$_2$, 0.0170 NaN$_3$ and 0.5% Triton X-100.

Further experimentation was carried out to determine the components or units forming the 5.9 million aggregate. In each case, the molecular weight estimate was determined using gel permeation chromatography as described below.

Attempts were made to deaggregate the 5.9 million molecular weight protein into its largest polypeptide units.

Gel permeation chromatography of the receptor glycoprotein was carried out before and after the various treatments described below. (A protein concentration of approximately 1 mg/ml was used for each treatment.) In each case, the gel columns were equilibrated and eluted with appropriate solvents containing 0.5% Triton X-100. Standards of known molecular weight (DNA supercoiled) blue dextran, thyroglobulin, ferritin, aldolase and catalase) were gel-filtered through the columns and gels selected to resolve the approximate range of the molecular sizes of a protein marker. The $K_{av}$ (index of solute migration in gel chromatography) for each marker and for each receptor component was calculated from its elution volume. The molecular weights of the receptor components were determined from a standard curve of $K_{av}$ versus the molecular weights of the known protein markers.

Treatment with 1M NaCl overnight at 4° as well as with 2% SDS and 1% mercaptoethanol at 4° did not alter the molecular weight of the receptor protein aggregate. However, treatment with 2% SDS, at 100° for $1\frac{1}{2}$ min, deaggregated the 5.9 million molecular weight material into a plurality of a 280,000 molecular weight species, which was separated on a Sepharose-6B column, of the hormone-free hLH-hCG receptor. The Sepharose-6B column was eluted with 0.1M acetic acid containing 1 mM MgCl$_2$, 0.01% NaN$_3$, 0.1% SDS and 0.5% Triton X-100. When the 280,000 molecular weight species was incubated with $^{125}$I-hCG, and, applied to a Sepharose-6B column, a major hormone-bound component with a molecular weight of 185,000 was recovered by elution with 10 mM Tris-HCl buffer containing 1 mM MgCl$_2$, 0.01% NaN$_3$ and 0.5% Triton X-100. If a molecular weight of 40,000 is subtracted for hCG from the 185,000 molecular weight species, the resulting molecular weight of 145,000 suggests the presence of a dimer of the receptor of approximately 280,000 molecular weight. That is, the 280,000 species disassociates into two oligomers of approximately 145,000 molecular weight each. Both the binding of $^{125}$I-hCG or covalent linking of $^{125}$I-hCG alone cause the reduction of the 280,000 molecular weight dimer, and the appearance of the hormone-bound 185,000 molecular weight forms of the receptor.

In another set of experiments, the 280,000 molecular weight component following treatment for $1\frac{1}{2}$ min at 100° with 2% SDS and 1.5 mM DTT (dithiothreitol) followed by gel filtration on a column of Ultrogel ACA-34, yielded a 120,000 molecular weight species of the hLH-hCG receptor by elution with a 0.01M Tris-HCl buffer containing 1 mM MgCl$_2$, 0.01% NaN$_3$, 0.01% SDS, 2 mM DTT and 0.5% Triton X-100. Further treatment of the 120,000 species with 50 mM DTT for $1\frac{1}{2}$ min at 100°, and gel filtration on Ultrogel ACA-34 in the above 0.01M Tris-MCl buffer yielded two oligomers of the molecular weights 85,000 and 38,000. Each of these components bound $^{125}$I-hCG specifically and eluted from Ultrogel ACA-34 by 10 mM Tris-HCl buffer containing 1 mM MgCl$_2$, 0.01% NaN$_3$ and 0.5% Triton X-100 as hormone-bound complexes of molecular weights of 125,000 and 92,000, respectively.

In another experiment, $^{125}$I-hCG was coupled covalently to the 5.9 million molecular weight aggregate, which was then dissociated into hormone-bound 185,000 molecular weight species, by treatment with 2% SDS, for $1\frac{1}{2}$ min. at 100°. A 3000 rpm supernate thereof was applied to a column of Sepharose-6B and in addition the sediment was redissolved in 10 mM Tris-HCl buffer containing 0.5% Triton X-100 and then treated with 2% SDS for $1\frac{1}{2}$ minutes at 100° C. followed by gel filtration on the same type column. In both instances, the 185,000 molecular weight species was obtained by elution with 10 mM Tris-HCl buffer containing 1 mM MgCl$_2$, 0.01% NaN, 0.1% SDS and 0.5% Triton X-100.

Treatment of the $^{125}$I-hCG coupled species with 50 mM DTT for $1\frac{1}{2}$ min at 100° also yielded $^{125}$I-hCG-coupled oligomers of the molecular weights of 110,000 and 74,000 (corresponding to 70,000 and 34,000 molecular weight units after subtracting 40,000 for hCG) Treatment of the 85,000 and 38,000 molecular weight units with up to 150 mM DTT in the presence of 2% SDS for 1½ min at 100°, did not dissociate these units further into smaller molecular weight components. Hence, it is expected that the 70,000 to 85,000 and the 34,000 to 38,000 molecular weight species are probably the disulfide linked subunits of the 120,000 to 145,000 molecular weight component and may be the smallest intact polypeptide units which carry out the specific binding with hCG and hLH.

From the above experiments and discussion, the two lowest molecular weight units known at this time of the naturally-occurring receptor may be defined with respect to their freedom from hormone units, their molecular weight ranges of about 34,000 to 38,000 and about 70,000 to 85,000, respectively, their specific binding capability for hCG and their stability under the various conditions of treatment heretofore described. In turn, these basic units appear to be linked through covalent disulfide bonds into repeating units of about 120,000 to 145,000 molecular weight. At the present time, it is believed that one each of the two types of basic units join to form the 120,000 to 145,000 molecular weight unit. Variations in molecular weight determinations are believed due to the limitations of the disc gel electrophoresis and gel chromatography systems, including the number of different standard protein markers employed. However, the important determinations are that two different molecular weight subunits, each having specific hCG binding capability exist which in turn form the basic repeating building blocks of the receptor. The 120,000 to 145,000 molecular weight species is in a sense a repeating monomeric unit, two of which link to form a 240,000 to 280,000 molecular weight oligomer. A plurality of these oligomers are associated with one another to form the 5.9 million aggregates.

Amino acid and carbohydrate analyses were carried out on the electrophoretically pure receptor product and on some of the partially purified intermediate receptor products. Amino acid analysis was carried out by dialyzing 100 mg aliquots of receptor overnight against water, drying in vacuo and hydrolyzing with 100 ml of 5.7N HCl at 110° for 24 h. The hydrolysate was dried again in vacuo to remove any residual acid. The sample was dissolved in citrate buffer, and analyzed for amino acids on an automatic amino acid analyzer (Durrum, Model D-500).

The neutral sugar content of the hLH-hCG receptor was determined by methanolysis of the sugars, trimethysilylation and gas liquid chromatography. The hexosamine content was determined on the amino acid analyzer after a 4 hour hydrolysis of the sample with 5.7N HCl. The sialic acid content of the purified receptor was determined by the thiobarbituric acid method.

The major amino acids found in the electrophoretically pure receptor are aspartic acid and glutamic acid. On a percentage basis, there is somewhat less of each in comparison with a sample purified by the sequential method of Example 1 but substituting affinity chromatography for zone electrophoresis. The carbohydrate content of the electrophoretically pure receptor is approximately 10%. See Table 1 setting forth amino acid and carbohydrate analysis of three receptor materials. The number of each type of amino acid residue in the glycoprotein aggregate can be calculated from Table 1.

The electrophoretically pure glycoprotein receptor aggregate acts as an antigen when administered to test animals, such as rabbits, for production of antiserum. It is believed that the various glycoprotein subunits of the aggregate, as disclosed hereinbefore, would also elicit antigenic response in test animals.

TABLE 1

AMINO ACID AND CARBOHYDRATE ANALYSES OF THE hLH-hCG RECEPTOR

| Amino Acid | Ultrogel ACA-34* | Affinity Chromatography** | Zone-electrophoresis (present invention without final immunoaffinity chromatography step) |
|---|---|---|---|
| | 9/100 g Protein | | |
| ASPARTIC | 8.7 | 9.4 | 9.1 |
| THREONINE | 4.0 | 5.6 | 5.3 |
| SERINE | 3.9 | 4.6 | 5.8 |
| GLUTAMIC | 13.6 | 12.6 | 12.1 |
| PROLINE | 9.0 | 8.7 | 5.2 |
| GLYCINE | 3.8 | 4.7 | 4.5 |
| ALANINE | 4.6 | 5.4 | 4.8 |
| VALINE | 6.0 | 5.1 | 8.3 |
| CYSTEINE | Not detectable | Not detectable | |
| Cysteic Acid | trace | 1.3 | 2.4$^a$ |
| METHIONINE | 1.5 | 1.7 | 2.3 |
| ISOLEUCINE | 4.9 | 5.5 | 4.4 |
| LEUCINE | 11.7 | 9.6 | 8.7 |
| TYROSINE | 3.4 | 4.3 | 4.9 |
| PHENYLALANINE | 5.1 | 6.0 | 5.0 |
| LYSINE | 7.3 | 6.9 | 7.0 |
| HISTIDINE | 3.6 | $^c$ | 2.8 |
| ARGININE | 7.5 | 7.6 | 7.4 |
| Carbohydrate | | | |
| Fucose | Not detectable | | Not detectable |
| Mannose | 1.2 | | 1.1 |
| Galactose | 0.7 | | 1.6 |
| N—acetylglucosamine | 1.1 | | 3.7 |
| N—acetylgalactosamine | 0.3 | | 2.6 |
| Sialic acid | 0.5 | | 1.9 |

$^a$Determined on a separate aliquot after performic acid oxidation
$^c$Eluted with detergent
*Intermediate sample of Example 1 type sequence up to and including the chromatographic step using Ultrogel ACA-34 but prior to further purification
**Example 1 type sequence carried out up to the chromatographic step using Ultrogel ACA-34 and followed by affinity chromatography instead of zone electrophoresis

EXAMPLE 2

This example illustrates one embodiment of the present invention involving the detection of the mid-cycle hLH surge.

A. Preparation of hormone-enzyme complex

Two mg of hLH were dissolved in 200 ml of 0.1M sodium phosphate buffer of pH 7.5 containing 0.1M NaCl and reacted with 200 ml of 20 mM N-succinimidyl 3,2-pyridyldithio-propionate (SPDP) in ethanol for 30 min at room temperature in a shaker. The excess SPDP was removed by gel-filtration on a 1×20 cm column of Sephadex G-25 (fine) in 0.01M ammonium bicarbonate buffer of pH 8.4. The column was eluted at the rate of 8.4 ml/hour in a refrigerated fraction collector via a Uvicord recorder. Each fraction was analyzed by standard radioimmunoassay to locate the hLH activity. 0.5 mg protein of the lyophilized fraction containing the 2-pyridyl-disulfide-hLH was reacted in a glass vial with 0.25 mg protein equivalent of thiolated alkaline phosphatase (i.e. 2.5 mM in 50 ml) for 24 h at room temperature with shaking. The incubate was applied to a 0.5×28 cm column of Ultrogel-ACA-34 equilibrated and eluted with 0.01M ammonium bicarbonate buffer of pH 8.4. Suitable aliquots of the fractions eluted from the column were analyzed by radioimmunoassay of hLH and examined for optical density at 420 nM in a Beckman spectrophotometer to locate hLH-alkaline phosphatase conjugate as well as unconjugated alkaline phosphatase and hLH. The fraction containing hLH-alkaline phosphatase conjugate was stored in suitable aliquots at −20° C. until use.

B. Preparation of inert support having anti-LH-q-globulin or purified receptor covalently coupled thereto Solid glass beads of 6 mm diameter were sandblasted with 60-grit particles at a pressure of 75 lb/sq inch for 10 min. A 0.001% solution of anti-hLH-q-globulin (1.4 mg/bead) and a 0.0035% aqueous solution of purified hLH-receptor protein of Example 1 (5 mg/bead) were used in the reaction. A batch of 200 g of the sandblasted beads (approximately 700 beads) was heated in 200 ml of 10% q-aminopropyl-triethoxysilane in toluene for 4 h at 70° C. in a Dubanoff metabolic shaker to generate alkylamino groups. The reagents were decanted; and the beads were washed three times with 200 ml aliquots of toluene, air dried, and incubated with 100 ml of 1.25% glutaraldehyde in 0.01M sodium phosphate buffer of pH 7.0 for 1 h at room temperature. The glutaraldehyde activated beads were washed 5–6 times with 100 ml aliquots of 0.01M sodium phosphate buffer of pH 7.0. The anti-LH-q-globulin was covalently coupled to glass beads as described by Post et al, supra. Similarly, the hLH receptor, in 0.01M Tris-HCl-buffer, pH 7.2, containing 0.5% Triton X-100, was coupled to the glass beads. After the coupling reaction, the beads were washed with chilled 0.01M sodium phosphate buffer to remove unreacted antibody or receptor. The beads were then incubated for 2 h at 4° C. with gentle shaking with 100 ml of 1M glycine solution in 0.01 sodium phosphate of pH 7.0 in order to block free alkylamino groups. The anti-hLH-q-globulin or hLH-receptor coupled beads were stored in air tight containers at −20° C. until use.

C. The actual assay procedure can be carried out in a conventional manner, for example using the following procedure to quantitatively determine hLH level.

Into two sets of 75×100 mm polystyrene assay tubes, each tube of one set containing one antibody coupled glass bead and each tube of the other set containing one receptor-coupled glass bead, there was added (1) 100 ml of low hLH containing urine (collected during the luteal phase and diluted 1:10 with phosphate buffer 0.01M, pH 7.0) as controls or an unknown urine sample as unknowns, (1:10 dilution); (2) 100 ml of hLH standard into the control tubes or sodium phosphate buffer into the unknown tubes and (3) 100 ml of LH-alkaline phosphatase conjugate equivalent to 150 ng protein/tube into all tubes. The urinary hLH standards contained doubling dilutions of hLH from 800 to 6.25 mIU/ml. The contents of the tubes were mixed and incubated for 2 h at room temperature on a Dubanoff shaker. After incubation the reagents were decanted and the beads were washed twice with 1 ml of 0.9% NaCl. One ml of substrate solution (6.3 mM p-nitrophenylphosphate-$Na_2$, 0.05M glycine and 0.5M $MgCl_2$ in 0.1N NaOH, pH 10.5) was added to each tube. The reaction was carried out for 30 min at 37° C., then 0.5 ml of 1N NaOH was added to each tube and the absorbance was recorded at 420 nM on a Beckman 2400 spectrophotometer. Standard curves were developed from the controls and the resulting standard curves used to determine the concentration of hLH in the unknowns.

The above illustrates both an enzymeimmunoassay (EIA) and an enzymereceptorassay (ERA) of hLH. The detection and analyses of hCG would be carried out in an analogous fashion using analogous reagents.

The sensitivity of the test, 11.0 to 12.5 mIU/ml, is sufficient to discriminate the midcycle hLH surge (75 to 100 mIU hLH/ml) of urine from hLH levels during follicular and luteal phases of normal menstrual cycles.

Two additional advantages arise through the use of the reagents and test procedure of this example. First, in the ERA, the stability of the purified receptor is increased after coupling to the inert support. Second, the EIA and ERA methods yield higher estimates for hLH than radioimmunoassay methods. This "amplification" characteristic increases as the level of hLH increases and in this manner the EIA and ERA methods serve as "amplifiers" to aid in the detection of the hLH surge.

In a preferred embodiment of the present invention, the hormone (hLH or (hCG)) used in the assay, i.e., to form the hormone-enzyme complex, is purified through use of the purified receptor to remove closely related hormones and subunits. Procedures such as those of Saito et al, supra, incorporated herein by reference, can be employed to accomplish hormone purification. For example, the hormone can be incubated with the receptor previously coupled to a solid phase; then the solid phase and supernatant are separated from one another and the hormone is dissociated from the receptor by treatment with a buffer at appropriate pH and temperature, e.g., 0.1M Tris-HCl buffer of pH 10, at 40° C. for 1 minute, to yield the purified hormone.

In the above example 2, the hLH-phosphatase conjugate was prepared through a reaction sequence of first reacting the hLH hormone with SPDP to form an hLH-SPDP complex through the N-succinimide ester group. Thereafter, the protein bound 2-pyridyl disulphide structure was reduced by the thiolated alkaline phosphatase. Chemically, the resultant molecule is a protein-protein complex linked through dithiopropionamide. Carlsson et al, supra, describes these types of chemical reaction sequences in detail.

A more preferred method of preparing the hormone-enzyme complex is to first react separately the hormone (hLH or hCG in this case) and the enzyme (non-thiolated) with SPDP to form a hormone-SPDP complex and an enzyme-SPDP complex. Thereafter, either the hormone-SPDP complex or the enzyme-SPDP complex is thiolated, for example by reaction with dithiothreitol in a 0.1M sodium acetate buffer. Finally, the thiolated reactant is reacted with the non-thiolated, i.e., hLH-SPDP complex is reacted with thiolated enzyme-SPDP complex. Except for the intermediate thiolation step, the reaction conditions can be those of Example 2.

In the above Examples, the inert support used in the solid phase assays of this invention has been exemplified by glass beads. Other inert supports known in the art could be employed, such as synthetic and natural polymers, other inorganic-based particles and so on, whether in the form of a bead or in other shapes such as a rod or strip, test tube, wafer, etc. Similarly, the hormone-enzyme complex has been exemplified with alkaline phosphatase, but other enzymes used in color-forming EIA or ERA reactions, such as horseradish peroxidase, glucuronidase, etc. are suitable herein.

A refinement and simplification of the present invention, particularly suitable for a qualitative at home ovulation or pregnancy test is to directly link a dye to the hormone. Thus, a hormone-dye complex is formed in place of the hormone-enzyme complex, using the procedures discussed above for forming the hormone-enzyme complex. A specific example of a hormone-dye complex is hLH coupled to the fluorescent dye ANS. This eliminates the need for a color-forming substrate. In this embodiment of the invention, the hormone-dye conjugate will be colored. If the conjugate is displaced from the solid phase by hLH in the unknown sample, the supernatant will become colored.

As variations of the invention, the following may be mentioned. For example, in embodiments to be used for carrying out the test procedures in the physician's office or at home, the antibody or receptor can be coupled directly to plastic test tubes, such as polystyrene tubes using procedures known in the art. The antibody or receptor can exist as a coating on a portion of the interior test tube surface. After addition of the hormone-enzyme conjugate, incubation and decantation are carried out. The substrate to form a color in the presence of the enzyme can then be added either to the original tube or to the supernatant to determine the presence or absence of ovulation and/or pregnancy. Another variation of the invention involves the use of a strip or rod, of plastic or glass, to which the antibody or receptor has been coupled. This solid phase is inserted into a test tube to which the hormone-enzyme or hormone-dye complex plus the unknown are added. Standard color-forming reactions are employed.

Biological fluids other than urine can be employed in the test procedures. For example, various blood fractions known to contain hLH and/or hCG can be used. In the "at-home" test embodiments, a convenient fluid to use is the saliva or urine.

As is understood in the art, standards and/or positive and/or negative controls will be run side-by-side with the unknown for comaprison purposes.

Variations of the invention will be apparent to the skilled artisan.

What is claimed is:

1. A process for preparing an hLH-enzyme complex or an hCG-enzyme complex which comprises a method selected from the group consisting of the following methods (A), (B) and (C):
   (A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;
   (B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and
   (C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex.

2. The product produced by the process of claim 1.

3. The process of claim 1, wherein said compound providing a reactive disulfide moiety is N-succinimidyl 3-(2-pyridyldithio)propionate.

4. The product produced by the process of claim 3.

5. A process for preparing an hLH-dye complex or an hCG-dye complex which comprises a method selected from the group consisting of the following methods (A), (B) and (C):
   (A) complexing hLH or hCG with a compound providing a reactive disulfide moiety, and reacting the complex with a dye containing an active thiol group to form a disulfide-linked hLH-dye complex or hCG-dye complex through thiol-disulfide exchange;
   (B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and
   (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex.

6. The product produced by the process of claim 5.

7. The process of claim 5, wherein the compound providing a reactive disulfide moiety is N-succinimidyl 3-(2-pyridyldithio)propionate.

8. The product produced by the process of claim 7.

9. A solid phase for an hLH or hCG-receptor assay comprising a solid, inert support carrying a gonadotropin receptor material containing a common receptor for hLH and hCG, wherein said material is prepared by the process comprising:
   (A) homogenizing a receptor source material in an aqueous medium to disperse the receptor in a liquid aqueous fraction;
   (B) separating and concentrating the liquid fraction;
   (C) fractioning the concentrate to separate at least one of inactive protein and lipid from the receptor;
   (D) re-dispersing the receptor in aqueous medium and extracting the aqueous medium with an organic solvent in which lipids are soluble to remove additional lipid from the aqueous phase;
   (E) separating the aqueous phase from the remainder of the product of step (D);
   (F) separating an hLH and hCG specific binding fraction of the receptor from adenyl cyclase and 5'-nucleotidase activity fractions of the receptor;
   (G) subjecting the hLH and hCG specific binding fraction of the receptor to electrophoresis to separate said fraction from other remaining protein fractions; and
   (H) recovering the resultant purified receptor.

10. The solid phase for an hLH or hCG receptor assay of claim 9, wherein said process additionally comprises, after step (H), the following step (I):
   (I) further purifying the receptor by subjecting it to immunoaffinity chromatography.

11. The solid phase of claim 9, wherein in said process:
(i) the receptor source material is bovine corpora lutea;
(ii) the concentration in step (B) is carried out by ultrafiltration to remove material below about 50,000 molecular weight;
(iii) the fractionation of step (C) is carried out by preparative sucrose linear density gradient ultracentrifugation, and before re-dispersion step (D), the active fraction is concentrated by ultrafiltration to remove sucrose and then centrifuged;
(iv) a detergent is used as a re-dispersion aid in step (D);
(v) in step (F), multi-stage chromatography is used to separate the adenyl cyclase and 5'-nucleotidase activity fractions and, wherein prior to step (G), the reactive fractions are ultrafiltered and gel-filtered to remove excess detergent; and
(vi) in step (G), vertical zone electrophoresis is carried out on a cellulose column and the active fractions are re-chromatographed.

12. The solid phase of claim 9, wherein in step (G) said electrophoresis is vertical-zone electrophoresis.

13. The solid phase of claim 9, wherein said gonadotropin receptor material has a binding capacity of at least 2,000 pM hCG/mg protein.

14. The solid phase of claim 9, wherein said support is selected from the group consisting of a glass bead, a test-tube, a strip and a rod.

15. A reagent kit comprising:
(A) a hormone-enzyme complex or a hormone-dye complex, wherein said hormone is selected from the group consisting of hLH and hCG;
(B) a solid phase comprising a solid, inert support carrying a gonadotropin receptor material containing a common receptor for hLH and hCG, wherein said receptor material is prepared by the process comprising:
(1) homogenizing a receptor source material in an aqueous medium to disperse the receptor in a liquid aqueous fraction;
(2) separating and concentrating the liquid fraction;
(3) fractioning the concentrate to separate at least one of inactive protein and lipid from the receptor;
(4) re-dispersing the receptor in aqueous medium and extracting the aqueous medium with an organic solvent in which lipids are soluble to remove additional lipid from the aqueous phase;
(5) separating the aqueous phase from the remainder of the product of step (4);
(6) separating an hLH and hCG specific binding fraction of the receptor from adenyl cyclase and 5'-nucleotidase activity fractions of the receptor;
(7) subjecting the hLH and hCG specific binding fraction of the receptor in electrophoresis to separate said fraction from other remaining protein fractions; and
(8) recovering the resultant purified receptor; and
(C) when a hormone-enzyme complex is employed, a material which forms a color when reacted with the enzyme of said hormone-enzyme complex.

16. The reagent kit of claim 15, wherein said process additionally comprises, after step (8), the following step (9):
(9) further purifying the receptor by subjecting it to an immunoaffinity chromatography.

17. The reagent kit of claim 15, wherein in said process:
(i) the receptor source material is bovine corpora lutea;
(ii) the concentration in step (2) is carried out by ultrafiltration to remove material below about 50,000 molecular weight;
(iii) the fractionation of step (3) is carried out by preparative sucrose linear density gradient ultracentrifugation, and before re-dispersion step (4), the active fraction is concentrated by ultrafiltration to remove sucrose and then centrifuged;
(iv) a detergent is used as a re-dispersion aid in step (4);
(v) in step (6), multi-stage chromatography is used to separate the adenyl cyclase and 5'-nucleotidase activity fractions and, wherein prior to step (7), the reactive fractions are ultrafiltered and gel-filtered to remove excess detergent; and
(vi) in step (7), vertical zone electrophoresis is carried out on a cellulose column and the active fractions are re-chromatographed.

18. The reagent kit of claim 15, wherein in step (7) said electrophoresis is vertical-zone electrophoresis.

19. The reagent kit of claim 5, wherein said gonadotropin receptor material has a binding capacity of at least 2,000 pM hCG/mg protein.

20. The reagent kit of claim 5, wherein the hormone-enzyme complex is the product produced by a method selected from the group consisting of the following methods (A), (B) and (C):
(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;
(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and
(C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex.

21. The reagent kit of claim 15, wherein the hormone-enzyme complex is the product produced by a method selected from the group consisting of the following methods (A), (B) and (C):
(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;
(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and (C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex, wherein said compound providing a reactive disulfide moiety is N-succinimidyl 3-(2-pyridyldithio)-propionate.

22. The reagent kit of claim 15, wherein said hormone-dye complex is the product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex.

23. The reagent kit of claim 15, wherein said hormone-dye complex is the product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex, wherein the compound providing a reactive disulfide moiety is N-succinimidyl 3-(2-pyridyldithio)propionate.

24. The reagent kit of claim 15, wherein said support is selected from the group consisting of a glass bead, a test-tube, a strip and a rod.

25. The reagent kit of claim 15, wherein the quantities of reagents are predetermined to provide a qualitative response to the presence or absence of sufficient hLH to indicate ovulation.

26. The reagent kit of claim 15, wherein the quantities of reagents are predetermined to provide a qualitative response to the presence or absence of sufficient hCG to indicate pregnancy.

27. The reagent kit of claim 15, wherein the hormone of said hormone-enzyme complex is prepared by the process comprising:

(1) contacting an impure hLH or hCG hormone with said a gonadotropin receptor material containing a common receptor for hLH and hCG under conditions to allow the hLH or hCG hormone to complex with said receptor;

(2) separating the receptor phase from the remainder; and (3) releasing the hLH or hCG from said receptor.

28. The reagent kit of claim 27, wherein complexation is carried out by admixing in an aqueous solution.

29. The reagent kit of claim 27, wherein said complexation is carried out by immunoaffinity chromatography.

30. A reagant kit comprising:

(A) a hormone-enzyme complex or a hormone-dye complex, wherein said hormone is selected from the group consisting of hLH or hCG;

(B) a solid phase comprisng a solid, inert support carrying an antibody to hLH or an antibody to hCG;

(C) when a hormone-enzyme complex is employed, a material which forms a color when reacted with the enzyme of said hormone-enzyme complex, wherein said hLH or hCG is prepared by the process comprising:

(1) contacting an impure hLH or hCG hormone with a gonadotropin receptor material containing a common receptor for hLH and hCG under conditions to allow the hLH or hCG hormone to complex with said receptor;

(2) separating the receptor phase from the remainder; and (3) releasing the hLH or hCG from said receptor, wherein said receptor material is prepared by the process comprising:

(a) homogenizing a receptor source material in an aqueous medium to disperse the receptor in a liquid aqueous fraction;

(b) separating and concentrating the liquid fraction;

(c) fractioning the concentrate to separate at least one of inactive protein and lipid from the receptor;

(d) re-dispersing the receptor in aqueous medium and extracting the aqueous medium with an organic solvent in which lipids are soluble to remove additional lipid from the aqueous phase;

(e) separating the aqueous phase from the remainder of the product of step (d);

(f) separating an hLH and hCG specific binding fraction of the receptor from adenyl cyclase and 5'-nucleotidase activity fractions of the receptor;

(g) subjecting the hLH and hCG specific binding fraction of the receptor to electrophoresis to separate said fraction from other remaining protein fractions; and (h) recovering the resultant purified receptor.

31. The reagent kit of claim 30, wherein said process additionally comprises, following after step (h), the step (i):

(i) further purifying the receptor by subjecting it to immunoaffinity chromatography.

32. The reagent kit of claim 30, wherein in said process:

(i') the receptor source material is bovine corpora lutea;

(ii') the concentration in step (b) is carried out by ultrafiltration to remove material below about 50,000 molecular weight;

(iii') the fractionation of step (c) is carried out by preparative sucrose linear density gradient ultracentrifugation, and before re-disperson step (d), the active fraction is concentration by ultrafiltration to remove sucrose and then centrifuged;

(iv') a detergent is used as a re-dispersion aid in step (d);

(v') in step (f), multi-stage chromatography is used to separate the adenyl cyclase and 5'-nucleotidase activity fractions and, wherein prior to step (g), the reactive fractions are ultrafiltered and gel-filtered to remove excess detergent; and (vi') in step (g), vertical zone electrophoresis is carried out on a cellulose column and the active fractions are re-chromatographed.

33. The reagent kit of claim 30, wherein in step (g) said electrophoresis is vertical-zone electrophoresis.

34. The reagent kit of claim 30, wherein complexation is carried out by admixing in an aqueous solution.

35. The reagent kit of claim 30, wherein said complexation is carried out by immunoaffinity chromatography.

36. The reagent kit of claim 30, wherein said gonadotropin receptor material has a binding capacity of at least 2,000 pM hCG/mg protein.

37. The reagent kit of claim 30, wherein the hormone-enzyme complex is the product produced by a method selected from the group consisting of the following methods (A), (B) and (C):

(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;

(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and (C) Separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex.

38. The reagent kit of claim 30, wherein the hormone-enzyme complex is the product produced by a method selected from the group consisting of the following methods (A), (B) and (C):

(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;

(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and (C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex, wherein said compound providing a reactive disulfide moiety is N-succinimidyl 3-(2-pyridyldithio)-propionate.

39. The reagent kit of claim 30, wherein said hormone-dye complex is the product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex.

40. The reagent kit of claim 30, wherein said hormone-dye complex is the product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex, wherein the compound providing a reactive disulfide moiety is N-succinimidyl 3-(2-pyridyldithio)propionate.

41. The reagent kit of claim 30, wherein said support is selected from the group consisting of a glass bead, a test-tube, a strip and a rod.

42. The reagent kit of claim 30, wherein the quantities of reagents are predetermined to provide a qualitative response to the presence or absence of sufficient hLH to indicate ovulation.

43. The reagent kit of claim 30, wherein the quantities of reagents are predetermined to provide a qualitative response to the presence or absence of sufficient hCG to indicate pregnancy.

44. A process for qualitatively or quantitatively determining the hLH or hCG level in an unknown sample comprising:

(A) admixing an inert, solid support carrying hLH or hCG receptor with an unknown sample, and an hLH-enzyme complex or hCG-enzyme complex, or hLH-dye complex or hCG-dye complex;

(B) incubating the resulting admixture of step (A) under conditions to allow the hLH or hCG to react with said receptor;

(C) separating the resulting solid phase from the resulting liquid phase;

(D) when an enzyme complex is used, adding a material which forms a colored compound in the presence of the enzyme to either the liquid phase or the solid phase;

(E) qualitatively or quantitatively measuring the amount of colored material produced, wherein when a quantitative measurement is made, comparing the amount of colored material produced with a standard curve to determine the quantitative result, wherein the receptor is a product produced by the process comprising:

(1) homogenizing a receptor source material in an aqueous medium to disperse the receptor in a liquid aqueous fraction;

(2) separating and concentrating the liquid fraction;

(3) fractioning the concentrate to separate at least one of inactive protein and lipid from the receptor;

(4) re-dispersing the receptor in aqueous medium and extracting the aqueous medium with an organic solvent in which lipids are soluble to remove additional lipid from the aqueous phase;

(5) separating the aqueous phase from the remainder of the product of step (4);

(6) separating an hLH and hCG specific binding fraction of the receptor from adenyl cyclase and 5'-nucleotidase activity fractions of the receptor;

(7) subjecting the hLH and hCG specific binding fraction of the receptor to electrophoresis to separate said fraction from other remaining protein fractions; and (8) recovering the resultant purified receptor.

45. The process of claim 44, wherein said process additionally comprises, after step (8), the following step (9):

(9) further purifying the receptor by subjecting it to immunoaffinity chromatography.

46. The process of claim 44, wherein in said process:

(i') the receptor source material is bovine corpora lutea;

(ii') the concentration in step (2) is carried out by ultrafiltration to remove material below about 50,000 molecular weight;

(iii') the fractionation of step (3) is carried out by preparative sucrose linear density gradient ultracentrifugation, and before re-dispersion step (4), the active fraction is concentrated by ultrafiltration to remove sucrose and then centrifuged;

(iv') a detergent is used as a re-dispersion aid in step (4);

(v') in step (6), multi-stage chromatography is used to separate the adenyl cyclase and 5'-nucleotidase activity fractions and, wherein prior to step (7), the reactive fractions are ultrafiltered and gel-filtered to remove excess detergent; and (vi') in step (7), vertical zone electrophoresis is carried out on a cellulose column and the active fractions are re-chromatographed.

47. The process of claim 44, wherein in step (7) said electrophoresis is vertical-zone electrophoresis.

48. The process of claim 44, wherein said gonadotropin receptor material has a binding capacity of at least 2,000 pM hCG/mg protein.

49. The process of claim 44, wherein said hormone-enzyme complex is the product produced by a method selected from the group consisting of the following methods (A), (B) and (C):

(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;

(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and (C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex.

50. The process of claim 44, wherein said hormone-enzyme complex is the product produced by a method selected from the group consisting of the following methods (A), (B) and (C):

(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;

(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and (C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex, wherein said compound providing a reactive disulfide moiety is N-succinimidyl 3-(2-pyridyldithio)-propionate.

51. The process of claim 44, wherein said hormone-dye complex is the product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex.

52. The process of claim 44, wherein said hormone-dye complex is the product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex, wherein the compound providing a reactive disulfide moiety is N-succinimidyl 3-(2-pyridyldithio)propionate.

53. The process of claim 44, wherein said support is selected from the group consisting of a glass bead, a test-tube, a strip and a rod.

54. The process of claim 44, wherein said hLH or hCG is prepared by the process comprising:

(1) contacting an impure hLH or hCG hormone with said a gonadotropin receptor material containing a common receptor for hLH or hCG under conditions to allow the hLH or hCG hormone to complex with said receptor;

(2) separating the receptor phase from the remainder; and (3) releasing the hLH or hCG from said receptor.

55. The process of claim 54, wherein complexation is carried out by admixing in an aqueous solution.

56. The process of claim 54, wherein complexation is carried out by immunoaffinity chromatography.

57. A process for qualitatively or quantitatively determining the hLH or hCG level in a unknown sample comprising:

(A) admixing an inert, solid support carrying hLH or hCG antibody with an unknown sample and an hLH-enzyme complex or hCG-enzyme complex or hLH-dye complex or hCG-dye complex;

(B) incubating the resulting admixture of step (A) under conditions to allow hLH or hCG to react with said antibody;

(C) separating the resulting solid phase from the liquid phase;

(D) when an enzyme complex is used, adding a material which forms a colored compound in the presence of the enzyme to either the liquid phase or the solid phase;

(E) qualitatively or quantitatively measuring the amount of colored material produced, wherein when a quantitative measurement is made, comparing the amount of colored material produced with a standard curve to determine the quantitative result, wherein said hLH or hCG is prepared by the process comprising:

(1) contacting an impure hLH or hCG hormone with said a gonadotropin receptor material containing a common receptor for hLH or hCG under conditions to allow the hLH or hCG hormone to complex with said receptor;

(2) separating the receptor phase from the remainder; and (3) releasing the hLH or hCG from said receptor, wherein said material is prepared by the process comprising:

(a) homogenizing a receptor source material in an aqueous medium to disperse the receptor in a liquid aqueous fraction;

(b) separating and concentrating the liquid fraction;

(c) fractioning the concentrate to separate at least one of inactive protein and lipid from the receptor;

(d) re-dispersing the receptor in aqueous medium and extracting the aqueous medium with an organic solvent in which lipids are soluble to remove additional lipid from the aqueous phase;

(e) separating the aqueous phase from the remainder of the product of step (d);

(f) separating an hLH and hCG specific binding fraction of the receptor from adenyl cyclase and 5'-nucleotidase activity fractions of the receptor;

(g) subjecting the hLH and hCG specific binding fraction of the receptor to electrophoresis to separate said fraction from other remaining protein fractions; and (h) recovering the resultant purified receptor.

58. The process of claim 57, wherein said process additionally comprises, after step (h), the following step (i):

(i) further purifying the receptor by subjecting it to an immunoaffinity chromatography.

59. The process of claim 57, wherein in said process:

(i') the receptor source material is bovine corpora lutea;

(ii') the concentration in step (b) is carried out by ultrafiltration to remove material below about 50,000 molecular weight;

(iii') the fractionation of step (c) is carried out by preparative sucrose linear density gradient ultracentrifugation, and before re-dispersion step (d), the active fraction is concentrated by ultrafiltration to remove sucrose and then centrifuged;

(iv') a detergent is used as a re-dispersion aid in step (d);

(v') in step (f), multi-stage chromatography is used to separate the adenyl cyclase and 5'-nucleotidase activity fractions and, wherein prior to step (g), the reactive fractions are ultrafiltered and gel-filtered to remove excess detergent; and (vi') in step (h), vertical zone electrophoresis is carried out on a cellulose column and the active fractions are re-chromatographed.

60. The process of claim 57, wherein in step (h) said electrophoresis is vertical-zone electrophoresis.

61. The process of claim 57, wherein complexation is carried out by admixing in an aqueous solution.

62. The process of claim 57, wherein said complexation is carried out by immunoaffinity chromatography.

63. The process of claim 57, wherein said gonadotropin receptor material has a binding capacity of at least 2,000 pM hCG/mg protein.

64. The process of claim 57, wherein said hormone-enzyme complex is the product produced by a method selected from the group consisting of the following methods (A), (B) and (C):

(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;

(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and (C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex.

65. The process of claim 57, wherein said hormone-enzyme complex is the product produced by a method selected from the group consisting of the following methods (A), (B) and (C):

(A) complexing hLH or hCG with a compound providing a reactive disulfide moiety, and reacting the complex with an enzyme containing an active thiol group to form a disulfide-linked hLH-enzyme complex or hCG-enzyme complex through thiol-disulfide exchange;

(B) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating the hLH-disulfide complex or hCG-disulfide complex and then reacting the thiolated complex with said enzyme-disulfide complex; and (C) separately complexing (1) hLH or hCG and (2) a non-thiolated enzyme to different portions of a compound providing a reactive disulfide moiety to form an hLH-disulfide complex or an hCG-disulfide complex, and an enzyme-disulfide complex, thiolating said enzyme-disulfide complex and then reacting the thiolated complex with said hLH-disulfide complex or said hCG-disulfide complex, wherein said compound providing a reactive disulfide moiety is N-succinimidyl 3-(2-pyridyldithio)-propionate.

66. The process of claim 57, wherein said hormone-dye complex is the product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex.

67. The process of claim 57, wherein said hormone-dye complex is a product produced by a method selected from the group consisting of the following methods (A), (B) and (C):

(A) complexing hLH or hCG with a compound providing a reactive disulfide moiety, and reacting the complex with a dye containing an active thiol group to form a disulfide-linked hLH-dye complex or hCG-dye complex through thiol-disulfide exchange;

(B) separately complexing (1) hLH or hCG and (2) a non-thiolated dye to different portions of a compound providing a reactive disulfide moiety to form an hLH-disulfide complex or an hCG-disulfide complex and a dye-disulfide complex, thiolating the hLH-disulfide complex or hCG-disulfide complex and then reacting the thiolated complex with said dye-disulfide complex; and (C) separately complexing (1) hLH or hCG and (2) a non-thiolated dye to different portions of a compound providing a reactive disulfide moiety to form an hLH-disulfide complex or an hCG-disulfide complex, and a dye-disulfide complex, thiolating said dye-disulfide complex and then reacting the thiolated complex with said hLH-disulfide complex or said hCG-disulfide complex, wherein the compound providing a reactive disulfide moiety is N-succinimidyl 3-(2-pyridyldithio)propionate.

68. The process of claim 57, wherein said support is selected from the group consisting of a glass bead, a test-tube, a strip and rod.

* * * * *